United States Patent
Petersen et al.

(10) Patent No.: US 10,542,355 B2
(45) Date of Patent: Jan. 21, 2020

(54) HEARING AID SYSTEM

(71) Applicant: Oticon A/S, Smørum (DK)

(72) Inventors: Eline Borch Petersen, Helsingør (DK); Thomas Lunner, Smørum (DK); Thomas Gleerup, Smørum (DK)

(73) Assignee: OTICON A/S, Smørum (DK)

( * ) Notice: Subject to any disclaimer, the term of this patent is extended or adjusted under 35 U.S.C. 154(b) by 0 days.

(21) Appl. No.: 16/217,831

(22) Filed: Dec. 12, 2018

(65) Prior Publication Data

US 2019/0182606 A1 Jun. 13, 2019

(30) Foreign Application Priority Data

Dec. 13, 2017 (EP) .................................... 17207008

(51) Int. Cl.
*H04R 25/00* (2006.01)
*A61B 5/0476* (2006.01)
(Continued)

(52) U.S. Cl.
CPC ....... *H04R 25/505* (2013.01); *A61B 5/04012* (2013.01); *A61B 5/0476* (2013.01);
(Continued)

(58) Field of Classification Search
CPC .............. H04R 25/505; H04R 2225/41; H04R 2225/67; A61N 1/36038; A61N 1/36036;
(Continued)

(56) References Cited

U.S. PATENT DOCUMENTS 6,134,474 A * 10/2000 Fischell ............... A61B 5/0476
607/45

2004/0193068 A1 * 9/2004 Burton ................. A61B 5/0476
600/544

(Continued)

FOREIGN PATENT DOCUMENTS

EP 3035710 A3 12/2003
EP 2744224 A1 6/2014
(Continued)

OTHER PUBLICATIONS

Petersen et al. "Hearing loss impacts neural alpha oscillations under adverse listening conditions", frontiers in Psychology, Feb. 2015, vol. 6, Article 177, p. 1-11.

*Primary Examiner* — Sean H Nguyen
(74) *Attorney, Agent, or Firm* — Birch, Stewart, Kolasch & Birch, LLP

(57) ABSTRACT

A hearing aid system includes an electric audio signal input, an audio input signal processing unit that is configured to process electric audio input signals in the first processing mode or in the second processing mode and to provide an electric audio output signal, and an output transducer. The hearing aid system further includes an audio input signal analysing unit that is configured to continuously monitor the electric audio input signal as a function of time and to determine and to provide a number of audio signal values each representing a characteristic of the electric audio input signal at a given time instance. The hearing aid system further includes a plurality of electrodes that are configured to be brought into contact with the skin of a user and which are configured—when operationally mounted to receive an electric signal that rep-resents a user's brain activity and to provide a respective EEG-related signal. The hearing aid system further includes an EEG-related signal analysing unit that is configured to continuously monitor the EEG-related signal as a function of time and to determine and to provide a number of EEG-related values each representing the EEG-related signal at a given time instance, a memory unit which is configured to store a number of audio signal values such that a first history of respective audio signal values is
(Continued)

created and/or to store a number of EEG-related values such that a second history of respective EEG-related values is created and a signal comparison unit that is configured to compare a current audio signal value with at least one preceding audio signal value of the first history to determine and to provide a deviation signal and/or to compare a current EEG-related value with at least one preceding EEG-related value of the second history to determine a measure of a user's current cognitive load and to provide a cognitive load representing output signal accordingly. The audio input signal processing unit is further configured to apply the first processing mode or the at least second processing mode depending on the deviation signal and/or depending on the cognitive load representing output signal.

20 Claims, 4 Drawing Sheets

(51) Int. Cl.
    *A61B 5/04*         (2006.01)
    *A61N 1/36*         (2006.01)
    *A61N 1/05*         (2006.01)
    *A61F 11/06*       (2006.01)

(52) U.S. Cl.
    CPC ....... *A61N 1/0529* (2013.01); *A61N 1/36036* (2017.08); *A61N 1/36038* (2017.08); *A61F 11/06* (2013.01); *H04R 2225/41* (2013.01); *H04R 2225/67* (2013.01)

(58) Field of Classification Search
    CPC .............. A61N 1/0529; A61B 5/04012; A61B 5/0476; A61F 11/06
    USPC ........................................................ 381/317
    See application file for complete search history.

(56) References Cited

U.S. PATENT DOCUMENTS

| | | | |
|---|---|---|---|
| 2009/0082829 A1* | 3/2009 | Panken | A61N 1/36139 607/45 |
| 2012/0010522 A1* | 1/2012 | Knudsen | H03M 3/486 600/544 |
| 2015/0164361 A1* | 6/2015 | Lunner | H04R 25/02 600/379 |
| 2016/0008076 A1 | 1/2016 | Bencteux et al. | |
| 2018/0253275 A1* | 9/2018 | Helwani | G06F 3/165 |
| 2019/0052977 A1* | 2/2019 | Hannemann | A61B 5/0478 |
| 2019/0223747 A1* | 7/2019 | Chou | A61B 5/04012 |

FOREIGN PATENT DOCUMENTS

| | | |
|---|---|---|
| EP | 2950555 A1 | 12/2015 |
| EP | 3035710 A2 | 6/2016 |
| EP | 3064136 A1 | 9/2016 |
| WO | WO 03/099179 A1 | 12/2003 |
| WO | WO 2014/205327 A1 | 12/2014 |

* cited by examiner

HEARING AID SYSTEM

TECHNICAL FIELD

The invention relates to a hearing aid system and a method for processing an electric audio input signal.

BACKGROUND

A hearing aid system typically comprises an input transducer, an audio input signal processing unit and an output transducer. The input transducer can be a microphone and is configured to receive sound from an ambient environment and to convert the received acoustic signal into an electric audio input signal. In the audio input signal processing unit, the electric audio input signal is processed by applying a specific processing mode. After processing the electric audio input signal, the audio input signal processing unit provides an electric audio output signal which is received by the output transducer. The output transducer, subsequently, provides an output signal that is based on the electric audio output signal and that can be perceived as sound by a user of the hearing aid system.

In everyday life, hearing situations in view of ambient sound that a person faces can vary e.g. between a silent ambient environment, a normal noise level and a very noisy or loud ambient environment.

To provide that all important information such as speech intelligibility that are contained in the electric audio output signal are presented to a user of a hearing aid system in an appropriate way, an audio input signal processing unit typically comprises different processing modes for processing an electric audio input signal. Different processing modes typically implement a processing algorithm that at least in part is different to processing algorithms used in other processing modes. E.g., if the received sound contains a high noise level, the respective electric audio input signal can be processed using a different processing mode than a processing mode used for processing an electric audio input signal that is based on a received sound signal having a low noise level. Processing algorithms may use parameter values that can be set in a hearing aid setting procedure. Hearing aid settings are parameter value sets that determine the function of at least one processing algorithm in a processing mode.

Typically, hearing aid settings can be adjusted based on an estimated signal-to-noise ratio. If a high noise level is detected, a processing mode comprising a noise reduction algorithm can be applied for processing the electric audio input signal. Alternatively, or in combination with e.g. noise reduction, hearing aid settings can be adjusted towards turning on microphone directionality. If the detected noise level is low, the complexity of the applied processing mode can be reduced such that it can be expected that the power consumption is reduced.

However, it is known that the ability to understand speech or to filter speech information contained in a noisy signal varies considerably from listener to listener. This not only depends on a degree of a person's hearing impairment but also depends on the individual cognitive ability. Furthermore, speech comprehension can even vary with the time of a day as speech comprehension can be influenced by the level of fatigue/sleepiness or the current motivation of understanding speech. Consequently, applying different processing modes according to predefined threshold values, e.g. according to predefined threshold values of the signal-to-noise ratio, can sometimes be highly insufficient.

In recent years, researchers have focused on investigating the relationship between speech recognition and a person's cognitive load (see e.g. E. B. Petersen et al., Front Psychol. 2015; 6:177). The term "cognitive load" refers to the total amount of mental effort being used in a person's working memory. Due to the fact that a person's cognitive load typically increases with increasing difficulty of the listening task, the cognitive load has gained an increasing interest for applications in hearing aid devices. Consequently, there exist a variety of attempts of estimating a person's cognitive load and using said estimate for hearing aid applications.

In US 2016/008076 A1 a method of operating a hearing instrument is presented that inter alia comprises adapting the processing of an input signal in dependence of the estimate of the present cognitive load.

Different methods for estimating a person's current cognitive load have been suggested, such as by using electrodes that are placed on the surface of an in-the-ear part of a hearing aid device. The electrodes pick-up a low voltage signal from a user's brain to record the electric activity of the brain. The resulting electroencephalogram (EEG) displays measured voltage fluctuations over time.

EP 2950555 A1 discloses a hearing aid capable of monitoring a user's hearing ability over time. The described hearing aid comprises at least one electrode that is adapted to pick up a low voltage signal from a user's brain.

EP 2744224 A1 describes a system of operating a hearing system. The system comprises one or more electrodes for measuring the brain wave signals of a user wearing the hearing instrument.

SUMMARY

It is an object of the invention to provide an improved hearing aid system.

According to the invention, the object is achieved by a hearing aid system comprising
  an electric audio signal input for receiving an electric audio input signal,
  an audio input signal processing unit comprising a first processing mode and at least a second processing mode wherein the audio input signal processing unit is configured to process the electric audio input signal in the first processing mode or in the at least second processing mode and to provide an electric audio output signal,
  an output transducer that is configured to receive the electric audio output signal and to provide an output signal that can be perceived as sound by a user,
  an audio input signal analyzing unit that is configured to continuously monitor the electric audio input signal as a function of time and to determine and to provide a number of audio signal values each representing a characteristic of the electric audio input signal at a given time instance,
  a plurality of electrodes that are configured to be brought into contact with the skin of a user and which are configured—when operationally mounted—to receive an electric signal that represents a user's brain activity and to provide a respective EEG-related signal,
  an EEG-related signal analyzing unit that is configured to continuously monitor the EEG-related signal as a function of time and to determine and to provide a number of EEG-related values each representing the EEG-related signal at a given time instance,
  a memory unit that is configured to store a number of audio signal values such that a first history of respective audio signal values is created and/or to store a number of EEG-related values such that a second history of respective EEG-related values is created, a signal comparison unit that is configured to compare a current audio signal value with at least one preceding audio signal value of the first history to determine and to provide a deviation signal and/or to compare a current EEG-related value with at least one preceding EEG-related value of the second history to determine a measure of a user's current cognitive load and to provide a cognitive load representing output signal accordingly.

The audio input signal processing unit is further configured to apply the first processing mode or the at least second processing mode depending on said deviation signal and/or depending on said cognitive load representing output signal.

Preferably, the electric audio signal input is connected to an input transducer for receiving an incoming sound signal and for converting the received sound signal into an electric audio input signal. The input transducer can be microphone that can also be a directional microphone with two microphones or two sound inlets. Typically, the input transducer is configured to receive an incoming sound signal and to convert the received sound signal into an electric audio input signal.

Alternatively, the electric audio signal input can be connected to a signal receiver for wireless reception of electric audio signals, e.g. via Bluetooth etc.

The electric audio input signal is processed by the audio input signal processing unit by applying one out of at least two different processing modes. The processing modes of the number of processing modes differ in that at least a part of the processing function or processing algorithm is different to the other processing modes. This allows applying a specific processing mode in dependence on the type of electric audio input signal. The different types of electric audio input signal can comprise e.g. different noise levels or different signal-to-noise ratios. One processing mode can e.g. be a processing mode for use in an ambient environment with a typical noise level. Such processing mode can be considered as an everyday processing mode. If the ambient environment has an inherently high noise level, a processing mode comprising noise reduction can be applied. The different processing modes can differ from one another e.g. at least with respect to one of the gain applied to the electric audio input signal, frequency-depended filtering, frequency compression or shifting, directionality, noise reduction, different gain for different frequency bands etc.

By processing the electric audio input signal, the audio input signal processing unit generates an electric audio output signal. The electric audio output signal is received by an output transducer that is configured to provide an output signal that can be perceived as sound by a user.

In case the hearing aid system is a hearing aid device, the output transducer is a receiver that emits sound to stimulate a user's eardrum. A respective hearing aid system can be implemented e.g. as a behind-the-ear (BTE) hearing aid system which typically has the microphone arranged behind the ear of a user or as an in-the-ear (ITE) hearing aid system which typically has the microphone arranged in the ear of a user. In both cases a speaker is typically placed inside a user's ear canal to stimulate the eardrum.

The hearing aid system can also comprise an implantable part such as in case of a cochlea implant or an auditory brainstem implant. Relating to a cochlea implant, the output transducer can be an electrode array comprising a number of electrodes for stimulating the cochlea nerve with electric pulses. If the hearing aid system is an auditory brainstem implant, the output transducer is configured to use electric stimulation to stimulate the brainstem of a user. In all cases, the output signal provided by the output transducer can be perceived as sound by a user.

The audio input signal analyzing unit continuously monitors the electric audio input signal as a function of time. Based on the analyzed electric audio input signal the audio input signal analyzing unit determines a number of audio signal values each representing a characteristic of the electric audio input signal at a given time instance. Characteristics of the electric audio input signal can be e.g. a signal-to-noise ratio which can be provided together with the corresponding time instance. Hence, for a series of time instances an evolution of the signal-to-noise ratio or other characteristics of the electric audio input signal can be provided.

The hearing aid system comprises a number of electrodes that can be arranged in an electrode array or separated from each other. The actual number of electrodes used can vary and can range from a single or two electrodes to a larger number. The electrodes can be located on the surface of an external or an internal part of a hearing aid device. When the hearing aid system is operationally mounted, the electrodes are brought into contact with a user's skin. Electrodes can also be located on the skull of a user or on wearable glasses. When the electrodes are operationally mounted they are configured to receive an electric signal, typically a low voltage signal such as an electroencephalogram (EEG) that represents a user's brain activity. Based on the received electric signal the electrodes can provide a respective EEG-related signal. The EEG-related signal can be the alpha activity, phase-coherence across time or a spatial distribution of a brain activity. The alpha activity sometimes also referred to as alpha wave is the normal bursts of electric activity from the cerebral cortex of a drowsy or inactive person, occurring at a frequency of about 8 to 12 Hz and is detectable with an EEG. Preferably, the low voltage signal that is picked-up by the electrodes is amplified by an amplifier to provide an amplified brain signal.

The EEG-related signal can be continuously monitored as a function of time by the EEG-related signal analyzing unit. For a number of time instance, the EEG-related signal analyzing unit determines EEG-related values each representing the EEG-related signal at a given time instance. Accordingly, the EEG-related signal analyzing unit can provide EEG-related values each with a corresponding time instance such that an evolution of EEG-related values can be monitored over a given time duration.

As aforementioned, the audio input signal analyzing unit provides audio signal values at given time instances and the EEG-related signal analyzing unit provides EEG-related values at given time instances. Both, the audio signal values and the EEG-related values can be stored in the memory unit. By storing a number of audio signal values each corresponding to a given time instance, a first history of respective audio signal values is created. The first history comprises a list of audio signal values each with corresponding time information such that the first history displays an evolution of audio signal values over time. Furthermore, by storing a number of EEG-related values each corresponding to a given time instance, a second history of respective EEG-related values is created. The second history comprises a list of EEG-related values each with corresponding time information such that the second history displays an evolution of EEG-related values over time.

The signal comparison unit is connected to the memory unit and can access the stored information. The signal comparison unit is configured to compare a current audio signal value with at least one preceding audio signal value of the first history to determine and to provide a deviation signal. The current audio signal value can be the audio signal value that is most recently stored in the memory unit. Accordingly, a current audio signal value represents or approximates an audio signal value close to the actual characteristics of the electric audio input signal that is currently monitored by the audio input signal analyzing unit. A current audio signal value can be compared to at least one of the preceding audio signal values contained in the first history. Preferably, the current audio signal value can be compared to an audio signal value that was stored just before the current audio signal value. By comparing the current audio signal value with at least one preceding audio signal value the signal comparison unit can determine a deviation signal that can be subsequently provided for further processing.

The signal comparison unit is further configured to compare a current EEG-related value with at least one preceding EEG-related value of the second history to determine and to provide a measure of a user's current cognitive load and to provide a cognitive load representing output signal accordingly. The current EEG-related value can be the EEG-related value that is most recently stored in the memory unit. Accordingly, the current EEG-related value represents or approximates an EEG-related value close to the actual EEG-related signal that is currently monitored by the EEG-related signal analyzing unit. A current EEG-related value is compared to at least one of the preceding EEG-related values contained in the second history. Preferably, the current EEG-related value is compared to an EEG-related value that was stored just before the current EEG-related value. By comparing the current EEG-related value with at least one preceding EEG-related value the signal comparison unit determines a measure of a user's current cognitive load that can be subsequently provided as a cognitive load representing output signal for further processing. As aforementioned, the EEG-related value can be based on the alpha activity, the phase-coherence across time or the spatial distribution of a brain activity According to the invention, the audio input signal processing unit is further configured to apply the first processing mode or the at least second processing mode based on said deviation signal and/or based on said cognitive load representing output signal.

The inventors recognized that by applying different processing modes according to predefined thresholds, it is not possible to adapt the processing of an electric audio input signal to changing individual user needs.

However, by applying the first processing mode or the at least second processing mode based on said deviation signal and/or based on said cognitive load representing output signal the processing mode, it is possible to individually adapt the processing of an electric audio input signal to changing hearing situations that a user of the hearing aid system is confronted with. Both the deviation signal and the cognitive load representing output signal can provide an individual measure of when a specific processing mode should be applied to improve the hearing experience of a user of the hearing aid system. Accordingly, this can result in a user-individual application of different processing modes. A different processing mode is to be understood as a processing mode that at least in parts is different to the other processing modes. If for example the noise level in the ambient environment increases the deviation signal which can be based on a monitored signal-to-noise ratio can indicate that applying a processing mode including noise reduction can be beneficial for the user. Accordingly, if the measure of a user's current cognitive load increases e.g. due to increasing difficulty of a listening task or due to a decreasing motivation of understanding speech, the cognitive load representing output signal can indicate that applying a different processing mode can be beneficial for the user of the hearing aid system.

Thus, by using the electrophysiological measure of an EEG, it is possible to obtain an individual measure indicating when to apply a specific processing mode for example a processing mode comprising noise reduction or when to turn on microphone directionality can be beneficial for a user's hearing experience.

The invention includes the recognition that hearing-aid settings are traditionally adjusted based on an estimated signal-to-noise ratio of the external sound environment. However, the ability to understand speech in noise varies considerably between listeners, not only as an effect of hearing loss, but also with the individual cognitive abilities. Furthermore, speech understanding can even vary with the time of day, the level of fatigue/sleepiness, motivation etc. By utilizing the electrophysiological measures of EEG, it is possible to obtain an individual measure indicating exactly when hearing-aid helping systems such as noise reduction and microphone directionality should be turned on.

The degree of hearing loss correlates with the electrophysiological measures of working-memory involvement (alpha activity in the EEG), indicating that the cognitive load increases in order to make up for the loss of hearing. A breakdown in alpha activity can be observed when increasing the difficulty of the listening task. Similar observations have been made in the functional magnetic resonance imaging (fMRI) activity of older adults as the difficulty of a visual task was increased. A similar breakdown behavior has been observed in pupil data, acting as a measure of cognitive load, as the signal-to-noise ratio was increased. When increasing listening difficulty by adding more background noise, an increase in pupil dilation is seen. However, at around 50% intelligibility the pupil dilation gradually decreased with more noise, until the pupil reached a size comparable to that observed at 100% intelligibility. Accordingly, the inventors suggest utilizing the breakdown-behavior of neural activity as an indicator of when hearing-aid helping systems should be turned on.

The interpretation of the breakdown behavior is two-fold. On one hand, it is considered to occur due to physiological constraints innately associated with neural activity and the allocation of cognitive resources, i.e., that the upper-limit of how many resources can be activated has been reached. Another possible explanation is based on the motivational intensity, stating that a person will invest more effort into overcoming a (listening) task when the difficulty increases, but only if it is judged that it is possible to succeed in solving the task. In practice, this means that the point of breakdown is not only linked to the difficulty of the listening task, e.g., signal-to-noise ratio, but also depends on the internal motivation of the listener to solve the task.

Taking together, the point of breakdown can serve as a highly individualized indicator of when task difficulty and/or internal motivation are no longer sufficient to successfully overcome the listening situation. At this point, the listener benefits from the helping systems incorporated into modern hearing aids.

With respect to preferred embodiments, the audio input signal analyzing unit preferably is further configured to provide a number of audio signal values wherein each audio signal value represents a value of a parameter of the electric audio input signal at a given time instance. Parameters of the electric audio input signal inter alia are amplitude, frequency etc.

The characteristics of the analyzed electric audio input signal preferably comprise at least one of a signal-to-noise ratio, an amplitude, a frequency or a further characteristic or a combination thereof.

The audio signal analyzing unit preferably is configured to continuously monitor the electric audio input signal and to continuously determine and provide the number of audio signal values during hearing aid system operation. Continuous monitoring is preferred over a monitoring that only occurs from time to time.

In a preferred embodiment, the EEG-related signal analyzing unit is configured to continuously monitor the EEG-related signal and to continuously determine and provide the number of EEG-related values during hearing aid system operation. Again, continuous monitoring is preferred over a monitoring that only occurs from time to time.

The EEG-related signal preferably is a signal that represents alpha activity, phase-coherence across time or spatial distribution of brain activity or a further EEG-related signal.

With respect to the arrangement of electrodes, it is preferred if the hearing aid system comprises an internal and an external part wherein the number of electrodes are located on the surface of the external and/or the internal part. In particular, it can be beneficial to provide electrodes on both, the internal and the external part in order to improve signal quality and/or to enable the detection of signal propagation vectors. Electrodes can for instance also be located on wearable glasses and/or on the scalp of a user.

In preferred embodiments, further sensors or electrodes can be provided, for instance: electrodes for capturing electrocardiogram signals, electrode for capturing electrooculogram (EOG) signals for monitoring eye movements or a further EEG-related signal or a combination thereof for estimating a cognitive load.

The audio input signal processing unit preferably is configured to apply the first processing mode or the at least second processing mode or a combination thereof depending on whether a breakdown point in the cognitive load representing output signal is detected or not. The breakdown points in the cognitive load representing output signal is detected if the magnitude of the current EEG-related value is smaller than the magnitude of at least one preceding EEG-related value stored in the second history.

In a further preferred embodiment, the audio input signal processing unit is configured to cause switching of the processing mode not only upon detection of a breakdown point but also upon detection of stagnation.

The audio input signal processing unit preferably is configured to apply the first processing mode or the at least second processing mode depending on whether the magnitude of the current EEG-related value is smaller than the magnitude of at least one preceding EEG-related value stored in the second history or not.

Alternatively, or additionally, the audio input signal processing unit may be configured to apply the first processing mode or the at least second processing mode depending on whether EEG-related signal analyzing unit detects a breakdown of alpha activity Alternatively, or additionally, the audio input signal processing unit may be configured to apply the first processing mode or the at least second processing mode depending on whether the determined deviation signal indicates an increase in the listening difficulty.

Preferably, the first and the second processing mode differ with respect to noise-reduction algorithm and/or activating or deactivating a directionality of the input transducer.

The output signal provided by the output transducer can be a sound signal generated by a loudspeaker or stimulation pulses provided by a stimulation unit of a cochlear implant.

In a preferred embodiment, the signal comparison unit is further configured to evaluate whether or not the measure of a user's current cognitive load is increased or decreased after a change of a processing mode and to provide an output signal representing the evaluation result. Based on an evaluation of the cognitive load after changing a processing mode it is possible to check whether the change of the processing modes has led to the desired effect.

Optionally, the audio input signal processing unit can be further configured to iteratively adapt the applied processing mode to a hearing situation based on said deviation signal and/or based on said cognitive load representing output signal. The iterative adaptation can be used to implement a processing mode that is successively optimized towards a specific hearing situation.

In preferred embodiments, at least one processing mode implements an evolutionary processing algorithm that is configured to adapt the processing of said electric audio input signal to specific hearing situations based on said deviation signal and/or based on said cognitive load representing output signal. An evolutionary or adjustable processing algorithm is an algorithm that can be adjusted based on hearing aid settings, such that the processing of the adjustable processing algorithm is performed in a different way than before the adjustment.

In a preferred embodiment, the hearing aid system comprises at least one hearing instrument that comprises the audio signal input, the audio signal processing unit, the output transducer and the output transducer.

It is further preferred if the hearing aid system comprises two hearing instruments, each hearing instrument comprising at least one surface electrode.

The hearing instrument preferably further comprises a memory unit and a wireless data interface that is operatively connected to said memory unit.

Preferably, the hearing instrument is configured to wirelessly communicate with the audio signal analyzing unit via the wireless data interface. The wireless data interface preferably comprises a transmitter that is configured to transmit at least information about said electric audio output signal and/or the applied processing mode to an external device or to an external system.

The audio signal analyzing unit can be implemented with a server that is part of an external system being accessible via the wireless data interface. Information about said electric audio output signal and/or the applied processing mode can be sent directly to external system. The external system can also be a Smartphone having an application program (App) installed which can be configured to further send said information to a cloud service.

In a further preferred embodiment, the wireless data interface comprises a receiver that is configured to receive at least a hearing aid setting and/or a processing algorithm from an external device or from an external system such that the received hearing aid setting and/or the received processing algorithm can be applied for processing said electric audio input signal in said audio input signal processing unit. The received hearing aid setting and/or the received processing algorithm can be used e.g. to edit an existing processing mode applied by the audio input signal processing unit or to implement a new hearing aid setting and/or processing algorithm to process an electric audio input signal. Thereby, new processing features for processing an electric audio input signal can be introduced into the hearing aid system.

In an embodiment, the transmitter and the receiver are incorporated in a transceiver.

The hearing aid system may be a cochlear implant, a brainstem implant, hearing instrument, a hearing aid, a bone conduction hearing aid, a headset, an earphone, an ear protection device, an active ear protection system, a hands-free telephone system, a mobile telephone, a teleconferencing system, a public-address system, a karaoke system, a classroom amplification system or a combination thereof.

In a preferred embodiment, the external system is a computer or a computer system that implements at least one processing algorithm based on received information about an electric audio output signal and/or an applied processing mode and to transmit the at least one implemented processing algorithm and/or a processing algorithm and/or applied processing mode to at least one hearing aid system.

According to a further aspect a method for processing an electric audio input signal is provided. The method comprises the steps of
  receiving an electric audio input signal,
  processing the electric audio input signal in a first processing mode or in an at least second processing mode and providing an electric audio output signal,
  continuously monitoring the electric audio input signal as a function of time and determining and providing a number of audio signal values each representing a characteristic of the electric audio input signal at a given time instance,
  receiving an electric signal that represents a user's brain activity and providing a respective EEG-related signal,
  continuously monitoring the EEG-related signal as a function of time and determining and providing a number of EEG-related values each representing the EEG-related signal at a given time instance,
  storing a number of audio signal values such that a first history of respective audio signal values is created and/or storing a number of EEG-related values such that a second history of respective EEG-related values is created, and
  comparing a current audio signal value with at least one preceding audio signal value of the first history to determine and to provide a deviation signal and/or comparing a current EEG-related value stored in the memory unit with at least one preceding EEG-related value of the second history to determine a measure of a user's current cognitive load and to provide a cognitive load representing output signal accordingly, The method further comprises applying the first processing mode or the at least second processing mode depending on said deviation signal and/or based on said cognitive load representing output signal.

Additionally, or alternatively, the method comprises applying the first processing mode or the at least second processing mode depending on said deviation signal and/or depending on said cognitive load representing output signal or a combination of the first processing mode and the at least second processing mode.

Preferably, the method comprises evaluating whether or not the magnitude of the measure of a user's current cognitive load is increased or decreased after a change of a processing mode from a first processing mode to a second processing and to maintain the second processing mode if the current cognitive load is decreased.

The method preferably further comprises iteratively adapting the applied processing mode to a hearing situation based on said deviation signal and/or based on said cognitive load representing output signal. An iterative adaptation of a processing mode can be achieved by iteratively amend a parameter value used by a processing algorithm that is applied in the processing mode.

According to a further aspect, a data processing system is provided that comprises a processor and program code means adapted to cause the processor to perform the steps of the method as disclosed above.

The hearing aid system disclosed above can also implement a crowd-assisted signal processing adjustment. The hearing aid system comprises
  an electric audio signal input for receiving an electric audio input signal,
  an audio input signal processing unit configured to process the electric audio input signal by applying a processing algorithm and to provide an electric audio output signal,
  an output transducer that is configured to receive the electric audio output signal and to provide an output signal that can be perceived as sound by a user,
  a transceiver that is operatively connected to the audio input signal processing unit and that is configured
    to transmit at least information about the electric audio input signal along with information about the electric audio output signal and/or information about an applied processing algorithm to an external device or an external device system, and/or
    to receive at least a hearing aid setting and/or a processing algorithm from an external device or an external system,
wherein
the hearing aid setting, and/or a processing algorithm received by the transmitter is provided to said audio input signal processing unit and is applied for adjusting the processing of said electric audio input signal.

In a preferred embodiment said hearing aid system comprises a plurality of electrodes which are configured to be brought into contact with the skin of a user and which are configured—when operationally mounted—to receive an electric signal that represents a user's brain activity and to provide a respective EEG-related signal.

Optionally, the hearing aid system comprises a cognitive load evaluation unit that is configured to evaluate the EEG-related signal and to determine and provide a user's cognitive load representing output value.

Alternatively, or additionally, the hearing aid system comprises a sound environment characterization unit that is configured to analyse the electric audio input signal and to determine and provide an output value representing a change in an acoustic environment.

In an embodiment, the hearing aid system comprises a control unit that is operatively connected to the transceiver and to the audio input signal processing unit and that is configured to adjust the processing of the electric audio input signal based on the hearing aid setting and/or a processing algorithm received by the transceiver.

In a preferred embodiment, the control unit is operatively connected to the cognitive load evaluation unit and is configured to adjust the processing of the electric audio input signal based on the user's cognitive load representing output value.

Preferably, the control unit is operatively connected to the sound environment characterization unit and is configured to adjust the processing of the electric audio input signal based on the output value representing a change in an acoustic environment.

In an embodiment the hearing aid system comprises an adjustable processing algorithm that can be applied for processing said electric audio input signal wherein said adjustable processing algorithm can be adjusted via the control unit, based on a user's cognitive load representing output value and/or based on an output value representing a change in an acoustic environment and/or based on a hearing aid setting that is received by the transceiver.

In a preferred embodiment said hearing aid setting and/or said processing algorithm is received via the transceiver during hearing aid system operation.

Preferably, said control unit is configured to adjust the processing of the electric audio input signal during hearing aid system operation.

In an embodiment, the hearing aid system is a cochlear implant, a brainstem implant, hearing instrument, a hearing aid, a bone conduction hearing aid, a headset, an earphone, an ear protection device, an active ear protection system, a handsfree telephone system, a mobile telephone, a teleconferencing system, a public-address system, a karaoke system, a classroom amplification system or a combination thereof.

A further aspect refers to a computer system comprising at least one computer that is configured to receive data from at least one hearing aid system according to at least one of the preceding embodiments, wherein the data at least comprise information about an electric audio input signal along with information about an electric audio output signal and/or information about an applied processing algorithm and wherein the computer system comprises a training algorithm and/or a neural network that is configured to implement at least a hearing aid setting and/or a processing algorithm based on the received data and wherein the computer system is further configured to transmit the implemented hearing aid setting and/or a processing algorithm to at least one external device such as a hearing aid system.

An individual hearing aid system can be at least temporarily connected to the computer system.

The hearing aid system described above can also implement a method of realizing a crowd-assisted signal processing adjustment. The method of implementing a crowd-assisted signal processing adjustment comprises
  receiving an electric audio input signal,
  processing the electric audio input signal by applying a processing algorithm,
  providing an electric audio output signal,
  transmitting at least information about the electric audio input signal along with information about the electric audio output signal and/or information about an applied processing algorithm to an external device or an external device system, and/or
  receiving at least a hearing aid setting and/or a processing algorithm from an external device or an external device system,
  applying the received hearing aid setting and/or processing algorithm for processing said electric audio input signal,
  providing an output signal that can be perceived as sound by a user.

Typically, it is a very slow and somewhat haphazard procedure to develop and optimize a hearing aid algorithm. This is because of the long time it takes to carry out clinical tests and the inability to properly model how a hearing-impaired person perceives sound. A promising way of improving the procedure of developing a hearing aid algorithm is machine learning.

However, to efficiently apply machine learning requires a sufficient amount of training data. One way to obtain a sufficient amount of training data is crowdsourcing (Crowd Outsourcing). Typically, a user of a hearing aid system presses a button in an app on his Smartphone when the sound is "not good". However, this process is a tedious and inefficient procedure because already a large number of people must have used the function to train the system. However, in general users have no incentive to do this more than a few times, before they are disappointed about the performance of this function. Accordingly, it is of great advantage if no further action from the crowd is needed other than living their normal life.

A possible way to solve this problem is an algorithm implemented in the hearing aid system that detects if the brain has difficulties understanding e.g. speech or if it is struggling. The output of such an algorithm along with information about the audio input signal and the state of the hearing aid algorithms can be sent to a cloud service via an app on the user's Smartphone or directly from the hearing aid system to the cloud service.

This information can be used to train e.g. a deep neural network. Training data from a very large number of users can be collected in this way. Thus, the neural network is trained by the crowd in an automatic way.

The trained neural network can be used to send new and better settings and/or algorithms to a large number of users of a hearing aid system via their Smartphone app or directly from the cloud service to the hearing aid system. As a result, all users assist each other to achieve better hearing just by living their life.

The learning process can be enhanced by using evolutionary algorithms, meaning that slight adjustments are randomly made to learn which adjustments work best in a particular situation. Bigger adjustments can be made between different users to make sure that a global optimum is found. The adjustments can be parameters of human-created algorithms like those used today, or it can be changing weights of a neural network in the hearing aid or changing between different algorithms.

Other data such as location or nearby wireless devices (phones, wife access points, bag tags, POI tags, etc.) can also be used. Based on a location defined by e.g. the presence of a particular person's Smartphone, and the pitch of the person's respective voice, any user of a hearing aid system interacting with that person can be able to understand this particular person.

BRIEF DESCRIPTION OF DRAWINGS

The objects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each object may each be combined with any or all features of the other objects. These and other objects, features and/or technical effect will be apparent from and elucidated with reference to the illustrations described hereinafter in which:

DETAILED DESCRIPTION

Figure 1:
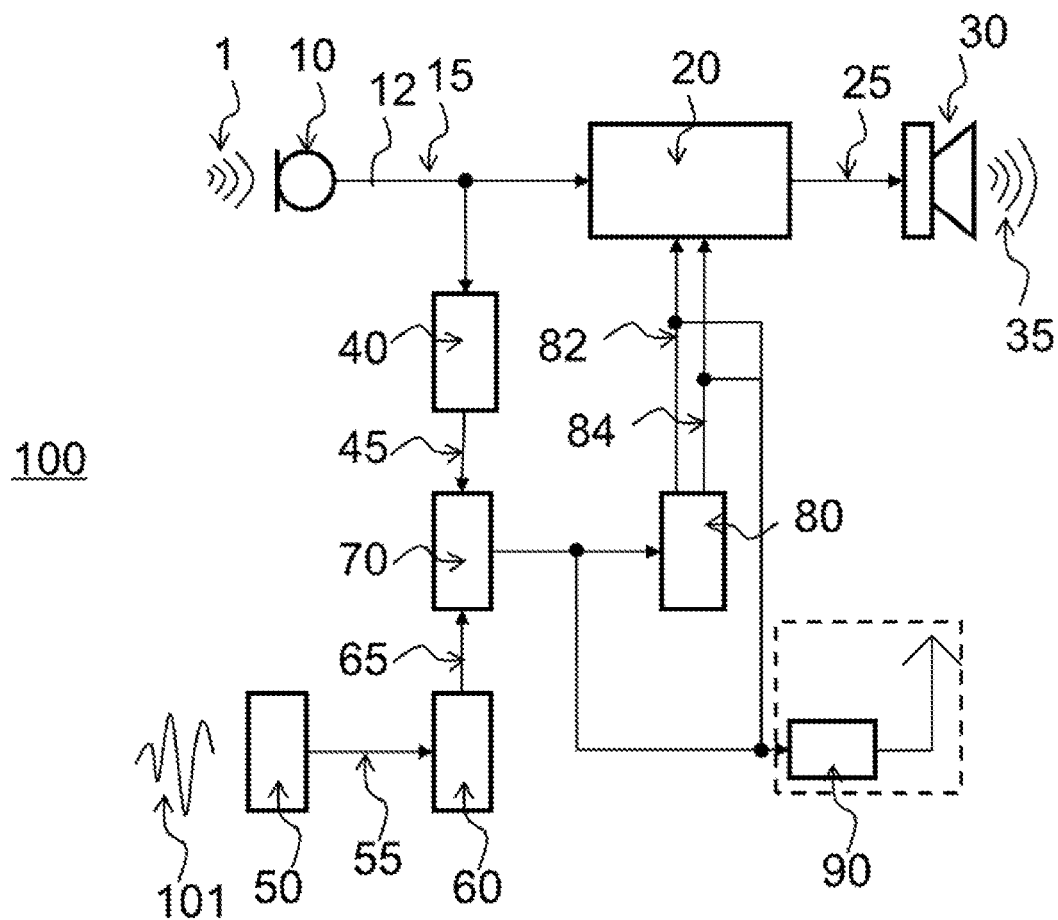
FIG. 1: is a schematic diagram of a hearing aid system according to the invention.

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several objects of the hearing device system and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

A hearing device may include a hearing aid that is adapted to improve or augment the hearing capability of a user by receiving an acoustic signal from a user's surroundings, generating a corresponding audio signal, possibly modifying the audio signal and providing the possibly modified audio signal as an audible signal to at least one of the user's ears. The "hearing device" may further refer to a device such as an earphone or a headset adapted to receive an audio signal electronically, possibly modifying the audio signal and providing the possibly modified audio signals as an audible signal to at least one of the user's ears. Such audible signals may be provided in the form of an acoustic signal radiated into the user's outer ear, or an acoustic signal transferred as mechanical vibrations to the user's inner ears through bone structure of the user's head and/or through parts of middle ear of the user or electric signals transferred directly or indirectly to cochlear nerve and/or to auditory cortex of the user.

The hearing device is adapted to be worn in any known way. This may include i) arranging a unit of the hearing device behind the ear with a tube leading air-borne acoustic signals or with a receiver/loudspeaker arranged close to or in the ear canal such as in a Behind-the-Ear type hearing aid or a Receiver-in-the Ear type hearing aid, and/or ii) arranging the hearing device entirely or partly in the pinna and/or in the ear canal of the user such as in a In-the-Ear type hearing aid or In-the-Canal/Completely-in-Canal type hearing aid, or iii) arranging a unit of the hearing device attached to a fixture implanted into the skull bone such as in Bone Anchored Hearing Aid or Cochlear Implant, or iv) arranging a unit of the hearing device as an entirely or partly implanted unit such as in Bone Anchored Hearing Aid or Cochlear Implant.

A hearing device may be part of a "hearing system", which refers to a system comprising one or two hearing devices, disclosed in present description, and a "binaural hearing system" refers to a system comprising two hearing devices where the devices are adapted to cooperatively provide audible signals to both of the user's ears. The hearing system or binaural hearing system may further include auxiliary device(s) that communicates with at least one hearing device, the auxiliary device affecting the operation of the hearing devices and/or benefitting from the functioning of the hearing devices. A wired or wireless communication link between the at least one hearing device and the auxiliary device is established that allows for exchanging information (e.g. control and status signals, possibly audio signals) between the at least one hearing device and the auxiliary device. Such auxiliary devices may include at least one of remote controls, remote microphones, audio gateway devices, mobile phones, public-address systems, car audio systems or music players or a combination thereof. The audio gateway is adapted to receive a multitude of audio signals such as from an entertainment device like a TV or a music player, a telephone apparatus like a mobile telephone or a computer, a PC. The audio gateway is further adapted to select and/or combine an appropriate one of the received audio signals (or combination of signals) for transmission to the at least one hearing device. The remote control is adapted to control functionality and operation of the at least one hearing devices. The function of the remote control may be implemented in a SmartPhone or other electronic device, the SmartPhone/electronic device possibly running an application that controls functionality of the at least one hearing device.

In general, a hearing device includes i) an input unit such as a microphone for receiving an acoustic signal from a user's surroundings and providing a corresponding input audio signal, and/or ii) a receiving unit for electronically receiving an input audio signal. The hearing device further includes a signal processing unit for processing the input audio signal and an output unit for providing an audible signal to the user in dependence on the processed audio signal.

The input unit may include multiple input microphones, e.g. for providing direction-dependent audio signal processing. Such directional microphone system is adapted to enhance a target acoustic source among a multitude of acoustic sources in the user's environment. In one object, the directional system is adapted to detect (such as adaptively detect) from which direction a particular part of the microphone signal originates. This may be achieved by using conventionally known methods. The signal processing unit may include amplifier that is adapted to apply a frequency dependent gain to the input audio signal. The signal processing unit may further be adapted to provide other relevant functionality such as compression, noise reduction, etc. The output unit may include an output transducer such as a loudspeaker/receiver for providing an air-borne acoustic signal transcutaneously or percutaneously to the skull bone or a vibrator for providing a structure-borne or liquid-borne acoustic signal. In some hearing devices, the output unit may include one or more output electrodes for providing the electric signals such as in a Cochlear Implant.

It should be appreciated that reference throughout this specification to "one embodiment" or "an embodiment" or "an object" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various objects described herein. Various modifications to these objects will be readily apparent to those skilled in the art, and the generic principles defined herein may be applied to other objects.

The claims are not intended to be limited to the objects shown herein but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follows.

FIG. 1 illustrates a hearing aid system 100 that is configured to record an electroencephalogram (EEG) and that can evaluate the recorded encephalogram in order to determine cognitive load and a breakdown point in the cognitive load in particular.

The hearing aid system 100 comprises a microphone 10 that is operatively connected to an electric audio signal input. The microphone 10 generates an electric audio input signal 15 that is fed to the electric audio signal input 12. In an alternative embodiment, an electric audio signal input can be connected to a signal receiver that is configured to wirelessly receive an electric audio input signal, e.g. via Bluetooth.

The electric audio input signal 15 received at the electric audio input signal 12 is fed to an audio input signal processing unit 20 that is configured to process the electric audio input signal and to provide an electric audio output signal 25 corresponding to the processed electric audio input signal. The audio input signal processing unit 20 is configured to provide at least two different processing modes. The processing modes may differ with respect to the application of gain, frequency filtering, frequency dependent gain, frequency shifting or compression, directionality etc.

The electric audio output signal 25 is fed to an output transducer 30 that is configured to receive the electric audio output signal and provide an output signal 35 that can be perceived as sound by a user. The output transducer can be a loud speaker that generates an output sound signal from the electric audio output signal. Alternatively, the output transducer can be a stimulation unit of a cochlear implant that generates stimulation pulses for stimulating the auditory nerve depending on the electric audio output signal.

The hearing aid system 100 further comprises an audio input signal analyzing unit 40 that is configured to continuously monitor the electric audio input signal 15 as a function of time and to determine and to provide a number of audio signal values 45 wherein each audio signal value represents a characteristic of the electric audio input signal 15 at a given time instance.

The hearing aid system 100 further comprises a number of electrodes 50 that are arranged and configured to contact the skin of a user when a hearing instrument of the hearing aid system is operationally mounted on the user. The electrodes are adapted to pick-up a low-voltage electric signal from the user's brain. The electric signals 110 that are picked up by electrodes 50 represent a user's brain activity. Thus, the electrodes 50 provide respective EEG-related signal 55. The EEG-related signal 55 can optionally be conditioned, for instance amplified and/or filtered and is fed to an EEG-related signal analyzing unit 60. The EEG-related signal analyzing unit 60 is configured to continuously monitor the EEG-related signal 55 as a function of time and to determine and provide a number of EEG-related values 65 wherein each EEG-related value 65 represents temporal characteristics of the EEG-related signal 55 at a given time instance. The hearing aid system further comprises a memory unit 70 that can store a number of audio signal values 45 such that a first history of respective audio signal values is created. Additionally, or alternatively, the memory unit 70 is configured to store a number of EEG-related values 65 such that second history of respective EEG-related values is created.

The hearing aid system further comprises a signal comparison unit 80 that can access the memory unit 70 and that is configured to compare a current audio signal value with at least one preceding audio signal value of the first history to thus determine and to provide a deviation signal 82 that represents temporal changes of the electric audio signal. Alternatively, or additionally, the signal comparison unit 80 is configured to compare a current EEG-related value with at least one preceding EEG-related value of the second history to determine a measure of a user's current cognitive load and to provide a cognitive load representing output signal 84 accordingly. When operated, the deviation signal 82 and the cognitive load representing output signal 84 are fed to the audio input signal processing unit 20. The audio input signal processing unit 20 in turn is configured to apply the first processing mode or the second processing mode depending on the deviation signal 82 and/or depending on the cognitive load representing output signal 84. Accordingly, the audio input signal processing unit 20 can apply an audio signal processing mode that possibly results in a lower cognitive load for the user. In other words, the hearing aid system according to FIG. 1 can switch between audio signal processing modes depending on the cognitive load of a user to thus ensure that the applied audio signal processing mode results in a reduced cognitive load of the user.

Optionally, the hearing aid system 100 comprises a transceiver unit 90 that is configured to transmit at least information about said electric audio output signal 25 and/or the applied processing mode to an external device or to an external system. The transceiver unit 90 can be further configured to receive at least a hearing aid setting and/or a processing algorithm from an external device or from an external system such that the received hearing aid setting and/or the processing algorithm. The received hearing aid setting and/or processing algorithm can be fed into the audio input signal processing unit 20 and subsequently applied for processing an electric audio input signal 15.

Figure 2:
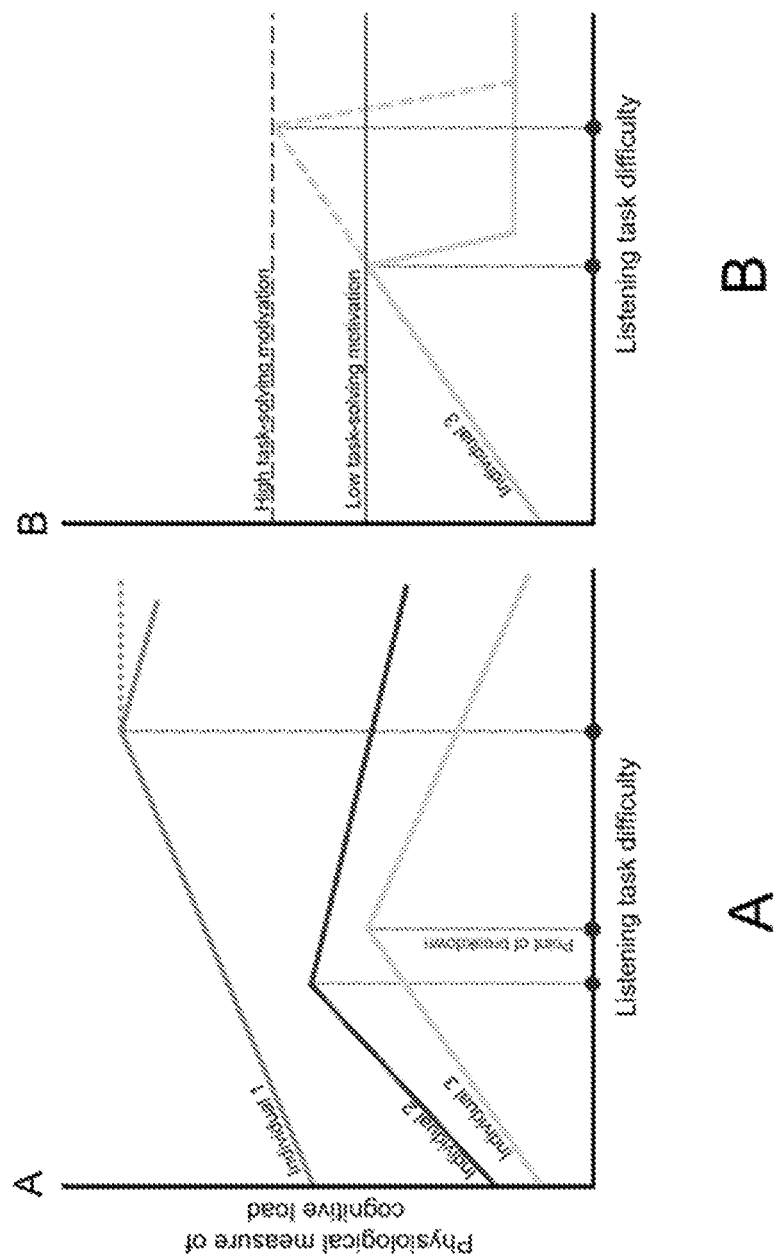
FIG. 2: is an illustration of three individuals' neural measure of cognitive load with increasing listening task difficulty.
Figure 3:
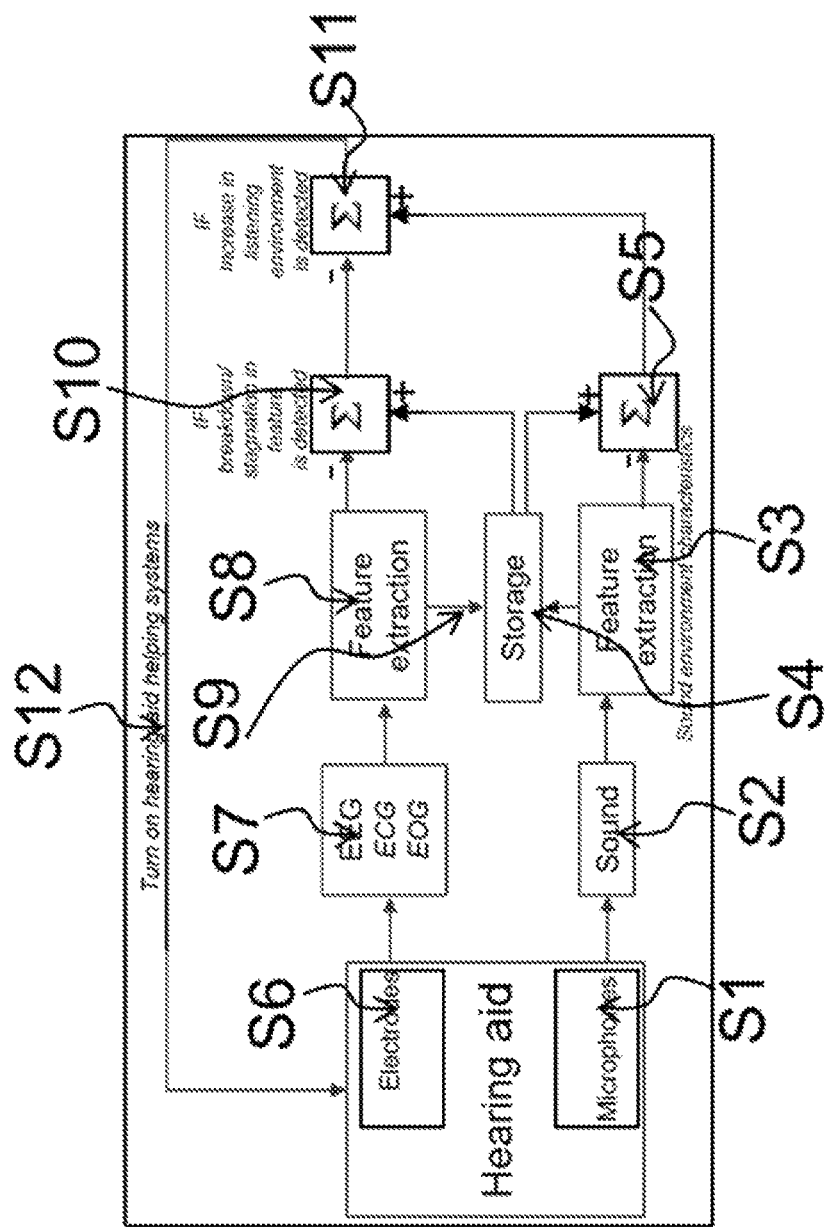
FIG. 3: is a schematic diagram of an implementation of a breakdown-detection system for hearing aid control.

Details of analyzing the signals captured by electrodes 50 as performed by the signal comparison unit 80 are now further illustrated with respect to FIGS. 2A, 2B and 3.

Breakdown behavior in neural measures of cognitive load can indicate the point at which an individual would benefit from hearing-aid helping systems. By continuously monitoring features of the EEG—i.e. features of the EEG-related signal 55 as captured by electrodes 50—including, but not limited to alpha activity, phase-coherence across time, and spatial distribution of brain activity, it is possible derive a measure of cognitive load.

As the characteristics of brain activity varies significantly between individuals, the absolute level of the EEG-feature is difficult to interpret in relation to a fixed threshold at which the listening task is believed to be too difficult. However, it can be assumed that the breakdown behavior resulting from an increasing listening task difficulty or the motivational threshold of the listener can be detected independent of the relative level of the EEG-feature.

In FIG. 2A it is illustrated how the overall level of the neural measure and the degree of change with increasing task difficulty can vary between individuals. A breakdown in neural activity as indicated by the dotted vertical lines is potentially to be independent of the absolute level of the neural activity or cognitive load. In fact, FIG. 2A illustrates three individuals' neural measure of cognitive load with increasing listening task difficulty. The breakdown in neural activity can differ from individual to individual as indicated by the dotted vertical lines. The individual breakdown points indicate when hearing-aid helping systems should be turned on for a user-individual improvement of the hearing experience. It is also possible that the neural measure exhibits stagnation, i.e., no change with increasing task difficulty, rather than a breakdown behavior. The scenario of stagnation is indicated by the dotted horizontal line shown for individual one.

Likewise, the internal motivation of the listener to overcome the listening task can vary depending on the situation and interest of a person, see FIG. 2B. Nevertheless, a detected breakdown in the cognitive load measure can indicate the point at which hearing-aid helping system can reduce the difficulty of the listening task and consequently improve the listening condition. FIG. 2B illustrates the difference in the individuals' motivation to solve a listening task. The point at which the listening task difficulty results in a breakdown in the cognitive load measure, again, is indicated by the dotted vertical lines. At a low level of motivation (lower solid horizontal line), the maximum level of invested effort is lower than if the individual is highly motivated (upper dashed horizontal line).

Technically, the EEG can be recorded from electrodes positioned inside the ear canal (EarEEG), on the surface of the internal or external part of a hearing aid, on wearable glasses, or on the scalp of the listener. Electrodes can capture not only EEG, but also heart rate (ECG and pulse) as well as eye-movements (EOG) potentially useful for estimating the cognitive load. The features preferably are stored together with information regarding the external sound environment available from the hearing-aid processing (see FIG. 3). This allows for continuously monitoring of the temporal dynamics of the cognitive load. By comparing the current cognitive load with the stored values from the time immediately preceding it, a breakdown (decrease) or stagnation (no change) in cognitive load can be detected. Upon detecting a breakdown/stagnation in cognitive load, it can be possible to compare this with potential changes detected in the sound environment. If a comparison between the current and previous sound environment show an increase in listening difficulty, or no change, this indicates that the listener can benefit from updating the hearing-aid settings. A breakdown-detection system as shown in FIG. 3 can potentially also be used for evaluating whether the change in hearing-aid settings have the desired effect of reducing the cognitive load. By applying an iterative process, it can be possible to gradually increase the aggressiveness or degree of the hearing-aid settings as to obtain the desired reduction in cognitive load. At the same time, the disadvantage of applying aggressive noise-reduction or full directionality of a hearing aid can be minimized.

FIG. 3 is a simplified diagram of the functional implementation of a breakdown-detection system for a hearing aid system 100. In a nutshell, the breakdown-detection system calculates the cognitive load and sound environment characteristics based on electrophysiological and auditory input. Detection of a breakdown in cognitive load is based on comparing the current estimation of cognitive load and sound environment with the preceding estimated values. If changes are detected, the hearing-aid settings are updated.

In more detail, the hearing aid system comprises an electric audio signal input for receiving and providing S1 an electric audio input signal. The electric audio input signal is continuously monitored S2 as a function of time. Based on the monitored electric audio input signal a number of audio signal values each representing a characteristic of the electric audio input signal at a given time instance are determined and provided S3. The number of audio signal values is stored S4 in a memory unit such that a first history of respective audio signal values is created. In a comparison unit a current audio signal value is compared S5 with at least one preceding audio signal value of the first history to determine and to provide a deviation signal. In the embodiment shown, the currently determined and provided audio signal value is compared to at least one preceding audio signal value of the first history to determine and to provide a deviation signal. In an optional embodiment, the audio signal value that is currently stored in the first history is compared to at least one preceding audio signal value of the first history to determine and to provide a deviation signal.

The hearing aid system 100 further comprises a number of electrodes for receiving S6 an electric signal that represents a user's brain activity and for providing a respective EEG-related signal. The EEG-related signal is continuously monitored S7 as a function of time. Based on the monitored EEG-related signal a number of EEG-related values each representing the EEG-related signal at a given time instance are determined and provided S8. The number of EEG-related values is stored S9 in a memory unit such that a second history of respective EEG-related values is created. In a comparison unit a current EEG-related value is compared S10 with at least one preceding audio signal value of the first history to determine and to provide a deviation signal. In the embodiment shown, the currently determined and provided S3 audio signal value is compared to at least one EEG-related value of the second history to determine a measure of a user's current cognitive load and to provide a cognitive load representing output signal accordingly. In an alternative embodiment, the EEG-related value that is currently stored in the first history is compared to at least one preceding EEG-related value of the second history to determine a measure of a user's current cognitive load and to provide a cognitive load representing output signal accordingly.

In a further step S11, it is evaluated whether an increase in the listening task difficulty resulting from the listening environment and/or an increase of a user's current cognitive load is detected. Subsequently S12, the information about a user's current cognitive load and the information about a current characteristics of electric audio input signal are fed into the audio input signal processing unit of the hearing aid system. Based on the deviation signal and/or based on the cognitive load representing output signal, a first processing mode or an at least second processing mode are applied to process the electric audio input signal.

Figure 4:
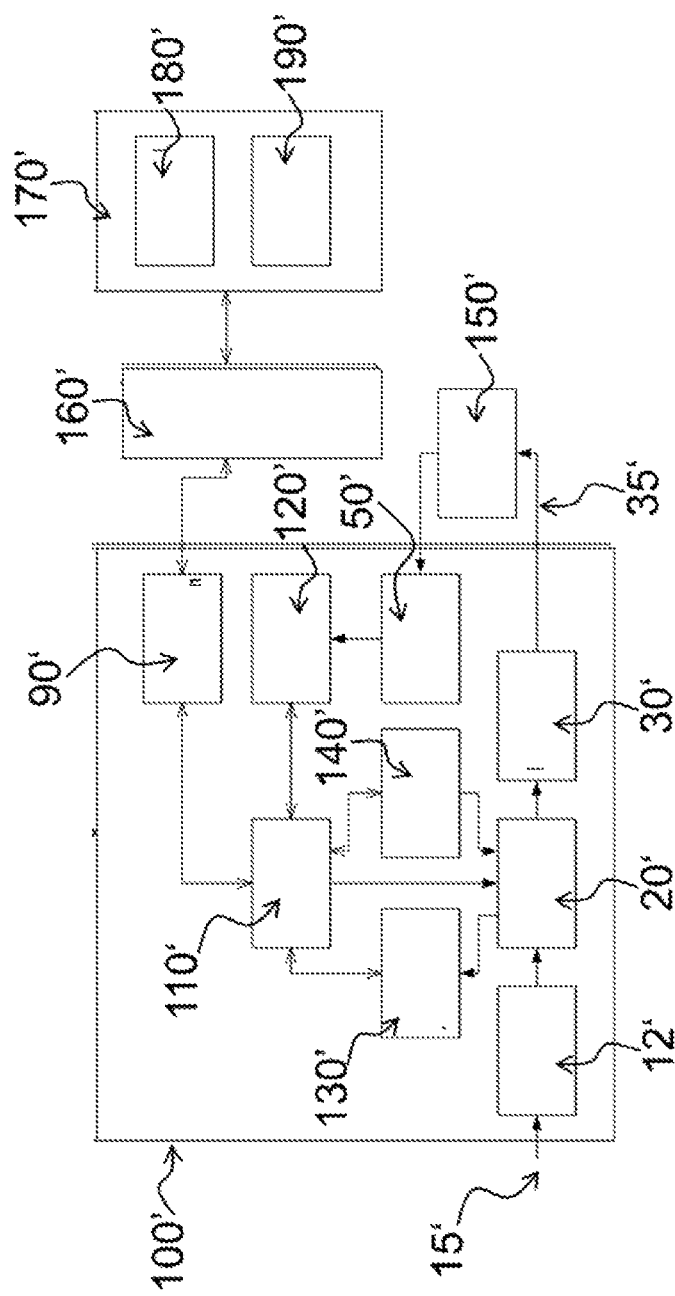
FIG. 4: is a schematic diagram implementation of a hearing aid system that implements crowed assisted signal processing adjustment.

FIG. 4 shows a schematic diagram of a hearing aid system 100' that implements crowd-assisted signal processing adjustment.

The hearing aid system 100' comprises an audio signal input 12' that is configured to receive an electric audio input signal 15'. The electric audio input signal 15' is fed to be processed in an audio input signal processing unit 20' and provided as an electric audio output signal. The electric audio output signal is delivered to an output transducer 30' which is configured to receive the electric audio output signal and to provide an output signal 35' that can be perceived as sound by a user 150'. The hearing aid system 100' comprises a number of electrodes 50' which are configured to be brought into contact with the skin of a user and which are configured—when operationally mounted—to receive an electric signal that represents a user's brain activity. The number of electrodes 50' provides a respective EEG-related signal that is evaluated via a cognitive load evaluation unit 120'. The cognitive load evaluation unit 120' can comprise an algorithm that detects whether the user 150' has difficulties of understanding e.g. speech.

A sound environment characterization unit 130' analyses the electric audio input signal 15' in order to detect changes in an acoustic environment. Changes in the acoustic environment can be e.g. an increase of the noise level. The information about changes in the acoustic environment and the information about the user's brain activity are both delivered to a control unit 110'. The control unit 110 is configured to control the audio input signal processing unit 20' and thus the processing of electric audio input signal 15'. In a first scenario, the control unit 110' delivers the information about changes in the acoustic environment and the information about the user's cognitive load directly to the audio input signal processing unit 20' which adjusts the processing according to the retrieved information. In a second scenario, the control unit 110' delivers the information about changes in the acoustic environment and the information about the user's cognitive load to modify an adjustable processing algorithm 140'. The adjustable processing algorithm 140' is applied to process the electric audio input signal 15' in the audio input signal processing unit 20'.

Furthermore, the control unit 110' communicates with a transceiver 90' that is configured to transmit at least information about an electric audio output signal provided by the audio input signal processing unit 20' and/or a processing algorithm applied by the audio input signal processing unit 20' to an internet gateway 160'. The transceiver 90' can also receive at least a hearing aid setting and/or a processing algorithm from the internet gateway 160' and transfer the received input to the control unit 110'. Accordingly, the received hearing aid setting and/or the processing algorithm can be applied for processing the electric audio input signal 15' in said audio input signal processing unit 20' or to adjust the adjustable processing algorithm 140'.

Through the internet gateway 160', the output of the processing algorithm along with information about the electric audio input signal 15 and the state of the hearing aid system algorithms is sent to a cloud service 170'. This can be done e.g. via an app on a user's Smartphone or directly from the hearing aid system to the cloud service 170'.'

This information is used to train e.g. a deep neural network 180'. Thereby, training data from a very large number of users can be collected. Thus, a neural network can be trained by the crowd in an automatic way. The trained neural network 180' can be used to send new and improved settings and/or algorithms to a number of users' of hearing aid systems e.g. via their Smartphone app or directly from the cloud to the respective hearing aid systems. As a result, all users assist each other to achieve a better hearing experience. Using training data, a training algorithm 190 can be improved towards certain hearing situations. Subsequently, the training algorithm 190 can be supplied to a number of hearing aid system users.

The process of adjusting the processing of an electric audio input signal to specific hearing situations can be enhanced by using evolutionary also called adjustable algorithms. For example, slight adjustments can be randomly made to learn which adjustments work best in a particular situation. Moreover, bigger adjustments can be made between different users to make sure a global optimum is found. Adjustments can be parameters of human-created algorithms like those commonly used today, or it can be changing weights of a neural network in a hearing aid system or changing between different algorithms.

The invention claimed is:

1. A hearing aid system comprising
an electric audio signal input for receiving an electric audio input signal,
an audio input signal processing unit that is operationally connected to said electric audio signal input and that is configured to apply one of a first processing mode and at least a second processing mode wherein the audio input signal processing unit is configured to process the electric audio input signal in the first processing mode or in the at least second processing mode and to provide an electric audio output signal,
an output transducer that is operationally connected to said audio input signal processing unit and that is configured to receive the electric audio output signal and to provide an output signal that can be perceived as sound by a user,
an audio input signal analyzing unit that is configured to continuously monitor the electric audio input signal as a function of time and to determine and to provide a number of audio signal values each representing a characteristic of the electric audio input signal at a given time instance,
a plurality of electrodes that are configured to be brought into contact with the skin of a user and which are configured—when operationally mounted—to receive an electric signal that represents a user's brain activity and to provide a respective EEG-related signal,
an EEG-related signal analyzing unit that is configured to continuously monitor the EEG-related signal as a function of time and to determine and to provide a number of EEG-related values each representing the EEG-related signal at a given time instance,
a memory unit that is configured to store a number of audio signal values such that a first history of respective audio signal values is created and/or to store a number of EEG-related values such that a second history of respective EEG-related values is created,
a signal comparison unit that is configured to compare a current audio signal value with at least one preceding audio signal value of the first history to determine and to provide a deviation signal and/or to compare a current EEG-related value with at least one preceding EEG-related value of the second history to determine a measure of a user's current cognitive load and to provide a cognitive load representing output signal accordingly,
wherein
the audio input signal processing unit is further configured to apply the first processing mode or the at least second processing mode depending on said deviation signal and/or depending on said cognitive load representing output signal.

2. A hearing aid system according to claim 1, wherein the audio input signal analyzing unit is further configured to provide a plurality of audio signal values each representing a value of a parameter of the electric audio input signal at a given time instance.

3. A hearing aid system according to claim 1, wherein the audio signal analyzing unit is configured to continuously monitor the electric audio input signal and to continuously determine and provide the number of audio signal values during hearing aid system operation.

4. A hearing aid system according to claim 1, wherein the EEG-related signal analyzing unit is configured to continuously monitor the EEG-related signal and to continuously determine and provide the number of EEG-related values during hearing aid system operation.

5. A hearing aid system according to claim 1, wherein the audio input signal processing unit is configured to apply the first processing mode or the at least second processing mode depending on whether the magnitude of the current EEG-related value is smaller than the magnitude of at least one preceding EEG-related value stored in the second history or not.

6. A hearing aid system according to claim 1, wherein the audio input signal processing unit is configured to apply the first processing mode or the at least second processing mode depending on whether said EEG-related signal analyzing unit detects a breakdown of alpha activity.

7. A hearing aid system according to claim 1, wherein the audio input signal processing unit is configured to apply the first processing mode or the at least second processing mode depending on whether the determined deviation signal indicates an increase in the listening task difficulty.

8. A hearing aid system according to claim 1, wherein the audio input signal processing unit is configured to apply the first processing mode or the at least second processing mode based on a comparison of the cognitive load representing output signal and the deviation signal.

9. A hearing aid system according to claim 1, wherein a processing mode comprises a noise-reduction algorithm and/or activating or deactivating a directionality of the input transducer.

10. A hearing aid system according to claim 1, wherein the signal comparison unit is further configured to determine whether or not the measure of a user's current cognitive is increased or decreased after a change of a processing mode and to provide a signal comparison unit output signal accordingly.

11. A hearing aid system according to claim 1, wherein the audio input signal processing unit is further configured to iteratively adapt the applied processing mode to a hearing situation based on said deviation signal and/or based on said cognitive load representing output signal.

12. A hearing aid system according to claim 1, wherein a processing mode comprises an evolutionary processing algorithm that is configured to adapt the processing of said electric audio input signal to specific hearing situations based on said deviation signal and/or based on said cognitive load representing output signal.

13. A hearing aid system according to claim 1, further comprising a transmitter that is configured to transmit at least information about said electric audio output signal and/or the applied processing mode to an external device or to an external system.

14. A hearing aid system according to claim 1, further comprising a receiver that is configured to receive at least a hearing aid setting and/or a processing algorithm from an external device or from an external system such that the received hearing aid setting and/or the processing algorithm can be applied for processing said electric audio input signal in said audio input signal processing unit.

15. A hearing aid system according to claim 1, wherein the hearing aid system is a cochlear implant, a brainstem implant, hearing instrument, a hearing aid, a bone conduction hearing aid, a headset, an earphone, an ear protection device, an active ear protection system, a handsfree telephone system, a mobile telephone, a teleconferencing system, a public address system, a karaoke system, a classroom amplification systems or a combination thereof.

16. A method for processing an electric audio input signal comprising
    receiving an electric audio input signal,
    processing the electric audio input signal in a first processing mode or in an at least second processing mode and providing an electric audio output signal,
    continuously monitoring the electric audio input signal as a function of time and determining and providing a number of audio signal values each representing a characteristic of the electric audio input signal at a given time instance,
    receiving an electric signal that represents a user's brain activity and providing a respective EEG-related signal,
    continuously monitoring the EEG-related signal as a function of time and determining and providing a number of EEG-related values each representing the EEG-related signal at a given time instance,
    storing a number of audio signal values such that a first history of respective audio signal values is created and/or storing a number of EEG-related values such that a second history of respective EEG-related values is created,
    comparing a current audio signal value with at least one preceding audio signal value of the first history to determine and to provide a deviation signal and/or comparing a current EEG-related value stored in the memory unit with at least one preceding EEG-related value of the second history to determine a measure of a user's current cognitive load and to provide a cognitive load representing output signal accordingly,
wherein the method further comprises
    applying the first processing mode or the at least second processing mode based on said deviation signal and/or based on said cognitive load representing output signal.

17. A method according to claim 16, wherein the method further comprises applying the first processing mode or the at least second processing mode based on said deviation signal and/or based on said cognitive load representing output signal or a combination of the first processing mode and the at least second processing mode.

18. A method according to claim 16, comprising evaluating whether or not the magnitude of the measure of a user's current cognitive load is increased or decreased after a change of a processing mode.

19. A method according to claim 16, comprising iteratively adapting the applied processing mode to a hearing situation based on said deviation signal and/or based on said cognitive load representing output signal.

20. A data processing system comprising a processor and program code means adapted to cause the processor to perform the steps of the method of claim 16.

* * * * *